United States Patent [19]

Luchaco

[11] 3,948,228

[45] Apr. 6, 1976

[54] EXHAUST GAS SENSOR OPERATIONAL DETECTION SYSTEM

[75] Inventor: David George Luchaco, Rochester, Mich.

[73] Assignee: The Bendix Corporation, Southfield, Mich.

[22] Filed: Nov. 6, 1974

[21] Appl. No.: 521,310

[52] U.S. Cl. ............... 123/32 EA; 60/276; 73/116; 340/52 R
[51] Int. Cl.² .......................................... B60Q 1/00
[58] Field of Search ...... 123/32 EA, 119 R; 60/276, 60/277, 285; 73/116; 340/52 R

[56] References Cited
UNITED STATES PATENTS

| | | |
|---|---|---|
| 3,837,165 | 9/1974 | Arriooni et al. ................... 60/277 |
| 3,851,469 | 12/1974 | Eichler ............................... 60/277 |
| 3,903,853 | 9/1975 | Kitler et al. ..................... 123/32 EA |

*Primary Examiner*—Charles J. Myhre
*Assistant Examiner*—Paul Devinsky
*Attorney, Agent, or Firm*—Russel C. Wells

[57] ABSTRACT

In a fuel injection system for internal combustion engines an exhaust gas sensor is periodically tested under controlled engine operating conditions for the purpose of detecting any failures in this sensor. The failure detection system generates an electrical signal in response to a failed sensor which signal is used to inform the engine operator of the failure of the sensor.

21 Claims, 5 Drawing Figures

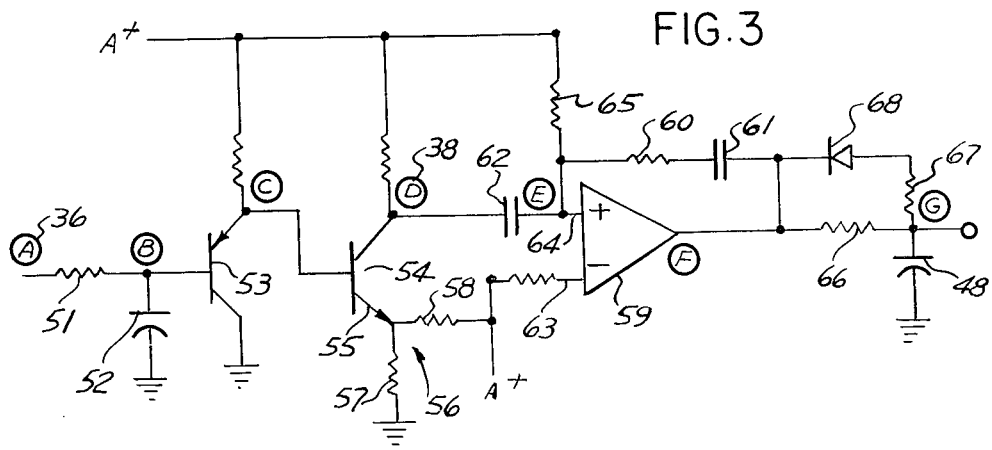
FIG. 3
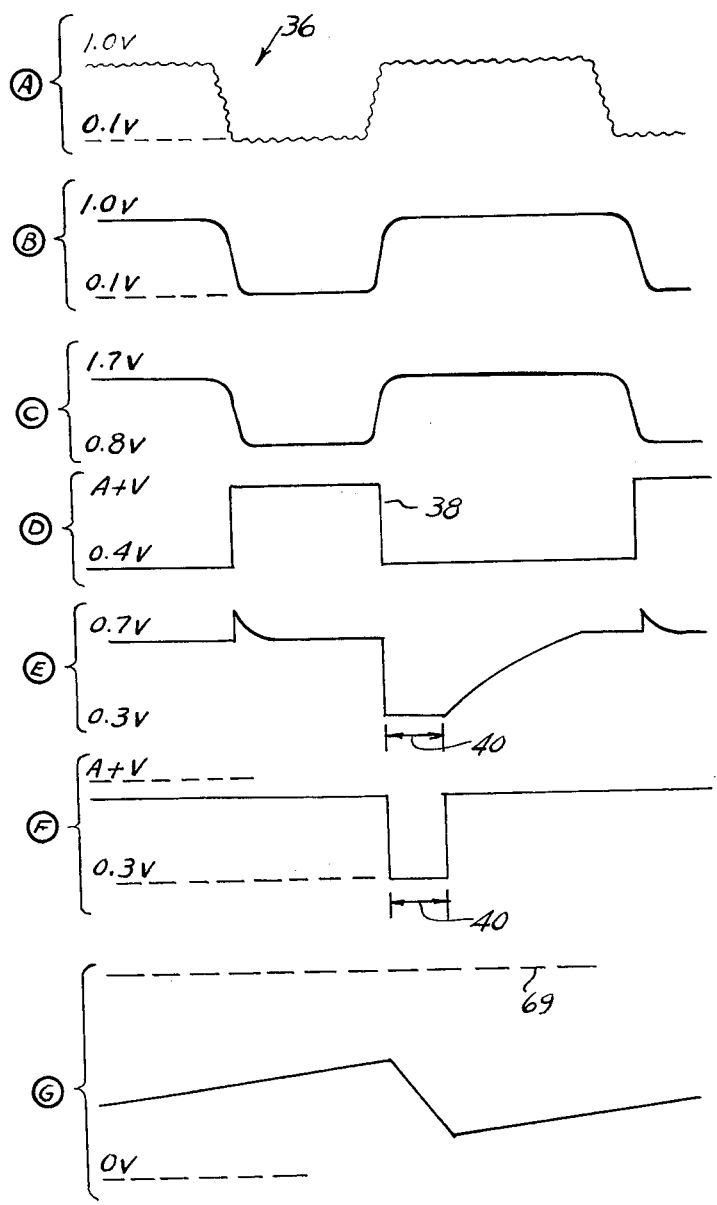

FIG. 4
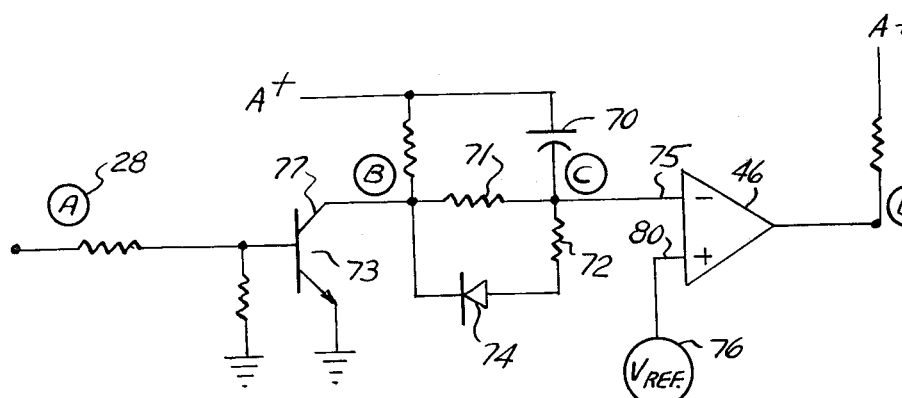
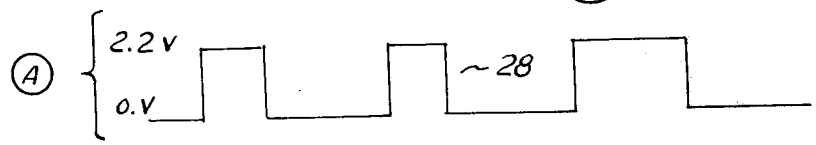
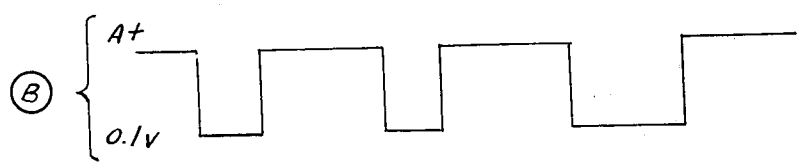
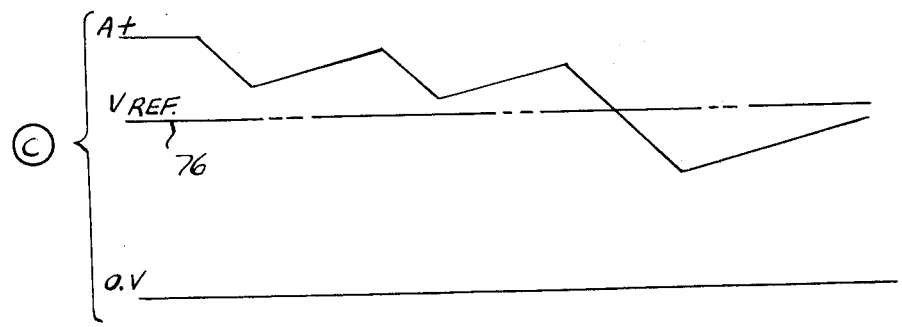
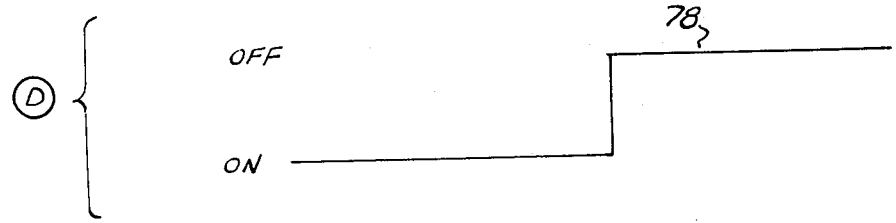

EXHAUST GAS SENSOR OPERATIONAL DETECTION SYSTEM

CROSS-REFERENCE TO RELATED APPLICATIONS

This application is related to application entitled "An Exhaust Gas Sensor Failure Detection System" by Junuthula Nirdosh Reddy having Ser. No. 510,277 and application entitled "Exhaust Gas Sensor Operating Temperature Detection System" filed by Alan L. Oberstadt having Ser. No. 510,276, both of which are assigned to the same assignee as is this application.

BACKGROUND OF THE INVENTION

1. Field Of The Invention

This invention relates to fuel injection systems in general and in particular to systems for detecting the failure of particular components of the system.

2. Description Of The Prior Art

The use of exhaust gas sensor in exhaust systems of internal combustion engines for controlling the air/fuel ratio to the engine is well known as exhibited in U.S. Pat. No. 3,745,768 issued to Zechnall et al. and entitled "Apparatus To Control The Proportion Of Air and Fuel In The Air/Fuel Mixture Of Internal Combustion Engines." In this particular patent an oxygen analyzer or exhaust gas sensor is responsive to the oxygen present in the exhaust gas of an internal combustion engine. A signal is generated by the sensor indicating whether or not oxygen is present in the exhaust gas and this signal is supplied to an electronic control unit for controlling or supplying information to control the amount of fuel injected into the cylinders of the internal combustion engine. If the sensor indicates that oxygen is present in the exhaust gas the sensor signal will supply information to the control unit to increase the amount of fuel supplied to the internal combustion engine. Conversely, if the sensor indicates a lack of oxygen in the exhaust gas it will supply information tending to reduce the amount of fuel supplied to the cylinder.

Such control is necessary for an internal combustion engine to improve the performance of the engine and to control the quality of the exhaust gas components in the exhaust gas of an internal combustion engine.

The use of exhaust gas sensors in the exhaust lines of furnaces is likewise old in the art. Again the purpose of such sensors in the exhaust lines is to control the operation of the furnace for better performance and economy.

Oxygen sensors are used in the steel making processes to determine the amount of oxygen contained in the molten steel in the process of manufacture. These sensors generate signals which are applied to a control unit to control the process in the steel making.

In such instances of the prior art, detection of a failed sensor has been primarily one of observation by an operator such as by the ultimate failure of a component such as a converter downstream of the sensor or the physical destruction of the sensor by the environment in which it is placed. Constant or periodic monitoring of the output voltage of the sensor under controlled conditions has been required in order to determine whether or not the sensor is operating or performing correctly.

In fuel management systems for internal combustion engines it is necessary to accurately control the fuel/air ratio entering the engine in order to control the products of combustion as they appear in the exhaust gases. It is desired in internal combustion engines to control the amount of unburnt hydrocarbons and carbon monoxides in the exhaust gas by regulating the fuel/air mixture to the cylinder of the engine. Nitrogen compounds in the exhaust gases are another undesirable component which may be neutralized by a catalytic converter placed downstream of the gas sensor. With the gas sensor controlling the fuel/air ratio into the engine thereby controlling hydrocarbons and carbon monoxide in the exhaust gas the catalytic converter need only have a single bed for neutralizing nitrogen compounds.

SUMMARY OF INVENTION

An exhaust gas sensor operational detection system is described having a waveshape transition detector means electrically responsive to the output signal of the exhaust gas sensor. The output of the detection means is electrically connected to a monostable multivibrator for generating a rectangular output pulse having a predetermined time duration which is independent of the pulse waveshape generated by the transition detector. The test control circuit means responsive to at least two predetermined engine operating conditions such as engine speed and engine temperature generated test enabled electrical signal for controlling when the detection system operates. Electrically connected and responsive to the multivibrator and enabled by the test control circuit means the transitional level indicator indicates by means of a voltage level on a storage capacitor the interval between successive transitions from the exhaust gas sensor. When the voltage level on the capacitor exceeds a predetermined level an indicator level sensor means generates a signal to a latching circuit. It is a function of the latching circuit to provide an alarm signal to the operator indicating the failure of the exhaust gas sensor for replacement or repair thereof.

DESCRIPTION OF THE DRAWINGS

In the Drawings

FIG. 3 is an electrical schematic including voltage waveforms of the transition detector, multivibrator and transition interval indicator circuits of FIG. 2;

FIG. 4 is a schematic including waveforms of the thermal time constant simulator of FIG. 2;

DETAILED DESCRIPTION

Figure 1:
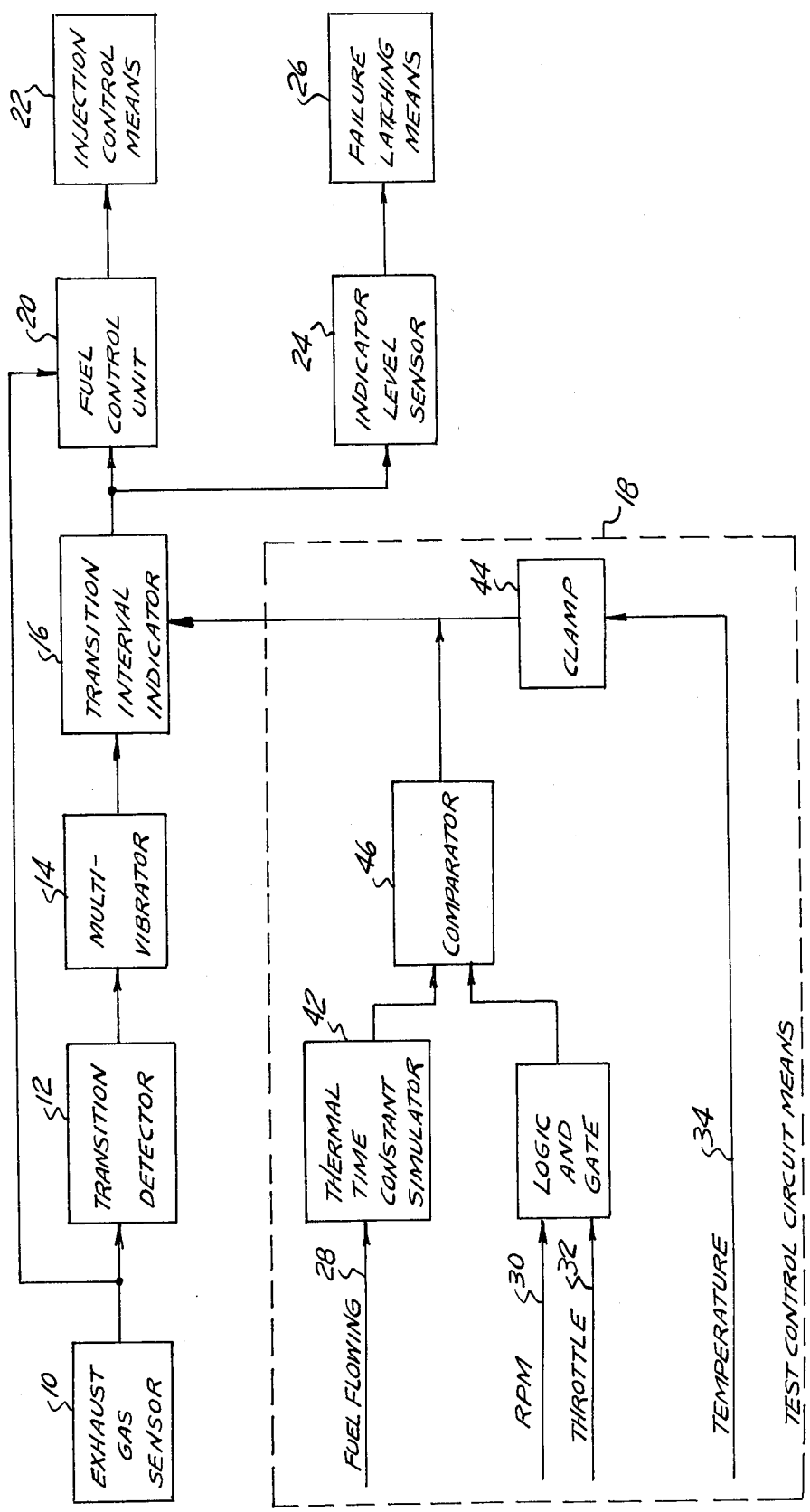
FIG. 1 is a block diagram of the sensor operational detection system as may be used in a fuel injection system for an internal combustion engine.

Referring to the FIGS. by the characters of reference there is illustrated in FIG. 1 a schematic of the preferred embodiment of the sensor operational detection system according to the present invention. The system comprises an exhaust gas sensor 10, a transition detector 12, a multivibrator 14, a transition interval indicator 16, a test control circuit means 18, a fuel control unit 20, an injection control means 22, an indicator level sensor 24, and a failure latching means 26. The test control circuit means 18 is responsive to at least one predetermined engine operating condition and in the preferred embodiment it is responsive to an electrical signal 28 representing fuel flowing, an electrical signal 30 representing the speed of the engine in RPM, an electrical signal 32 representing the throttle position, and an electrical signal 34 representing the engine temperature. In response to these four parameters a test enable signal is provided to the transition interval indicator 16.

In the system of FIG. 1, the exhaust gas sensor 10 is a sensor which is positioned in the exhaust system of an internal combustion engine and is responsive to the chemical composition of the exhaust gas flowing through the system. In the preferred embodiment the exhaust gas sensor 10 is an oxygen gas sensor which is capable of generating an output signal 36 having a first voltage level in the presence of oxygen in the exhaust gas and a second voltage level in the absence of oxygen in the exhaust gas. Such a signal is illustrated in the waveshape A of FIG. 3. Other gas sensors may be used that are responsive to other constituent gases or characteristics of the exhaust and in response to these particular characteristics will generate a voltage level signal having at least a first and second voltage level for indicating the presence or the relative amount or the proportion of the sensed parameter in the exhaust gas.

The output signal 36 of the exhaust gas sensor 10 is electrically connected to the transition detector 12 which is responsive to the shift in the voltage levels of the output signal 36 of the exhaust gas sensor 10. In response to the output signal 36 the transition detector 12 generates a first electrical signal 38 which is substantially a rectangular waveshape signal switching between greater voltage levels than the output signal 36 from the exhaust gas sensor 10. Such a signal is illustrated in the waveshape D of FIG. 3.

In the preferred embodiment, the output signal 38 of the transition detector 12 is electrically connected to a monostable multivibrator 14 which in the preferred embodiment is responsive to a negative trigger signal for generating a negative pulse. The pulse time duration 40 of the multivibrator output signal is independent of the pulse time duration of first electrical signal 38 from the transition detector 12.

The test control means of FIG. 1 in the preferred embodiment is responsive to the combination of four predetermined engine operating conditions. As will hereinafter be shown, the test enabling signal generated from the test control circuit means 18 is present only when the internal combustion engine is operated at predetermined operational conditions. One condition is that the engine must be up to operating temperature as determined by means such as a coolant temperature sensor not shown generating a temperature signal 34. Another condition is that the engine has been operating under a load condition for a sufficient period of time so that the thermal time constants of the several elements of the system will not have an adverse effect on the fuel flow processing in the engine. This condition is satisfied by the connection of the electrical signal 28 representing fuel flowing to the thermal time constant simulator 42 which is illustrated in detail in FIG. 4. After these two temperature considerations are satisfied the test control circuit means 18 is then responsive to the electrical signal 30 representing speed of the crankshaft of the engine which is generated by means of the circuit illustrated in FIG. 5.

In addition to the above temperature and speed conditions, it has been found that in order to accurately test an oxygen gas sensor 10 in the exhaust system of an internal combustion engine it is necessary that the test be conducted when the engine is in a reasonably steady state condition. This steady state condition is such that the system is responsive to controlled engine operation of the internal combustion engine thereby controlling the chemical composition of the exhaust gas. One such steady state condition is that of idle engine operation. Since an engine under a relatively heavy load may have the same crankshaft rotation as that in the idle condition, it is necessary to detect the position of the throttle valve to determine which of the two conditions prevail. In the test control circuit means 18, the throttle signal 32 is an electrical signal representing when the throttle valve is closed or not closed. In this manner therefore the system of FIG. 1 will test the operation of the exhaust gas sensor 10 during hot engine idle conditions and will detect failures only during this operational mode.

The transition interval indicator 16 is enabled by a signal from the clamp 44 and the comparator 46 of the test control circuit means 18 and is responsive to the output signal of the multivibrator 14. Since the multivibrator generates a signal each time that the exhaust gas sensor 10 makes the transition from the first voltage level to the second voltage level the transition interval indicator 16 indicates by means of a variable voltage stored on an indicator such as a capacitor means 48, the time between successive transitions. If the exhaust gas sensor 10 is working properly the interval between transitions is relatively short and the variable voltage level of the indicator 48 is relatively low. However, if the exhaust gas sensor 10 is not responsive to changes in the composition of the exhaust gas, the interval between transitions becomes great and the variable voltage level on the indicator 48 becomes higher and higher.

The output of the transition interval indicator 16 is electrically connected to a fuel control unit 20 which in turn generates electrical signals controlling the injection control means 22. The output of the injection control means controls one or more electrically operated fuel injectors or groups of injectors 50. The fuel control unit 20 responding to the output from the transition interval indicator 16 will vary in a predetermined relationship the timing of the fuel injector means. It is a function of these three units, 16, 20, and 22 to alter the injection time of at least one injector or one group of injectors in such a manner that the chemistry of the exhaust gas will change. In the preferred embodiment, the fuel control unit 20 will reduce the injection control time for the one injector or one group of injectors thereby causing a lean exhaust gas to flow past the exhaust gas sensor 10. In response to this lean exhaust gas the sensor 10 will generate a signal to the fuel control unit 20 in an attempt to enrichen the fuel mixture and position the exhaust gas composition on the rich side of stoichiometric point. It is this switching back and forth across the stoichiometric point which the exhaust gas sensor responds by generating its output signal 36 having first and second voltage levels. If the exhaust gas sensor 10 does not respond to the changes in the fuel mixture then the transition interval indicator 16 will generate by means of a high voltage signal on the capacitor means 48 that the interval between successive transitions is great.

This high voltage level is sensed by an indicator level sensor 24 and generates a signal to activate a failure latching means 26. Once activated, the failure latching means will generate a failure signal to warn the operator of the internal combustion engine that the exhaust gas sensor 10 is not operating properly. This failure signal may take many forms such as lights or buzzers in the operator's compartment of the internal combustion engine or may under certain conditions cause the internal combustion engine to malfunction. One such operating condition occurs at idle speed and the failure latching means, in an electronic fuel injection system having at least two groups of injectors, may cause one group of injectors to periodically misfire or not open thereby causing an extreme rough idle operating condition for the internal combustion engine. Such condition will be such that the internal combustion engine is capable of operating but it is sufficiently annoying to cause the operator to investigate and have the exhaust gas sensor 10 repaired or replaced.

Referring to FIG. 3, there is illustrated in schematic form the circuitry for the transition detector 12, the multivibrator 14, and the transition interval indicator 16. Additionally, FIG. 3 shows voltage waveshapes taken at several points in the circuitry which are identified by upper case letters. As previously indicated it is a function of these three units 12, 14 and 16 to respond to the operation of the exhaust gas sensor 10 to alter the injection time of at least one injector or one group of injectors in such a manner that the exhaust gas chemistry will change. The input signal labelled A is typical of the output signal 36 received from an exhaust gas sensor 10 or its associated amplifier. This pulse is applied through a filter network 51 and 52 to the input of an emitter follower transistor 53 in the transition detector 12. As shown by the pulse waveform B the resistor capacitor input filter 51, 52 removes the relatively high frequency signals or noise on the output signal 36 from the exhaust gas sensor 10. The output of the emitter follower transistor 53 labelled C, is supplied to the input of the second stage 54 of the transition detector. In the waveshapes of FIG. 3 the typical voltage levels for the signals are indicated. As therefore seen in the first stage 53, the output signal 36 of the exhaust gas sensor 10 drives the first stage 53 into saturation by the negative transition of the output signal from the sensor 10.

The second stage 54 of the transition detector 12 has its emitter 55 biased by a voltage divider 56 comprising a pair of resistors 57 and 58 electrically connected across the source of supply. In the preferred embodiment the voltage on the emitter 55 of the transistor 54 is approximately 200 millivolts. The output of the second stage 54 is a relatively sharp rectangular wave pulse 38 switching between the voltage level of the supply and the saturation voltage drop across the transistor 54 plus the bias on the emitter 55. It is a function of this second stage 54 to complete the shaping and raise the power gain of the signal 36 from the exhaust gas sensor.

The multivibrator stage in the preferred embodiment is a monostable or one-shot multivibrator formed from an integrated circuit comparator 59 and its feedback network comprising a series resistor 60 and capacitor 61. The output signal 38 of the second stage 54 of the transition detector is capacitively coupled by means of a capacitor 62 to the inverting input 63 of the comparator 59.

The noninverting input 64 of the comparator 59 is biased through a resistor 65 from the voltage source A+. With reference to waveshapes E and F on FIG. 3 it is seen that the multivibrator 14 is responsive to a negative trigger signal on its noninverting input 64 for generating a negative pulse. This negative pulse has a predetermined time duration 40 which is independent of the time duration of the input pulse 38 from the second stage 54 of the transition detector 16.

As illustrated in waveshape E, the input signal to the comparator 59 at its noninverting input 64 is charged back up to the supply voltage with a time constant which is determined by the resistance 60 in feedback circuit of the comparator and the series resistor 65 from the source of supply and the capacitor 61.

The transition interval indicator 16 in the preferred embodiment is an asymetrical integrator in that its charging and discharging paths are in parallel but operate with different time constants, It is the voltage level on the capacitor 48 which is sensed by the indicator level sensor 24 to determine or detect the failure of the exhaust gas sensor 10. The charging circuit for the capacitor 48 comprises a resistor 66 electrically connected to the ouput of the multivibrator 14 and through this resistor the capacitor 48 attempts to charge to the normally high voltage level output of the comparator 59. The discharging circuit for the capacitor 48 is a resistor 67 and a diode 68 electrically connected in series to the output of the comparator 59. However, the diode 68 is electrically connected in the circuit so as to block the flow of charging current to the capacitor 48. The respective values of the two resistors 66 and 67 determine the time constants for their respective circuit. In the preferred embodiment the discharge time constant is much smaller than the charging time constant. As an example the resistance value of the charging resistor 66 is 8 times the resistance value of the discharging resistor 67.

Referring to the waveshape G of FIG. 3 there is shown the slow charging voltage for the capacitor 48 which is determined by the charging resistor 66. In the preferred embodiment this time constant is approximately 15 seconds. When the multivibrator 14 generates its pulse illustrated in waveshape F the capacitor 48 discharges through its discharge network for the duration of the pulse. In the preferred embodiment the output pulse time 40 of the multivibrator 14 is approximately 40 milliseconds and the discharge time constant for the capacitor 48 is approximately 3 seconds.

Thus it is seen for the circuit illustrated in FIG. 3 with power applied to the circuit a capacitor 48 will attempt to charge up through its charging resistor 66 to the output of the comparator 59. Since the normal output of the comparator 59 is approximately equal to the source voltage, the voltage on the capacitor 48 would eventually be equal to the source voltage. However, as will hereinafter be shown, the test control circuit means 18 provides a clamping signal on the capacitor 48 preventing it from being charged. With an exhaust gas sensor 10 electrically connected to the input of the transition detector 12 and having a characteristic waveshape as shown in waveform A of FIG. 3 the capacitor 48 will attempt to discharge in response to positive going transition of the sensor output signal 36. For the purposes of failure detection a predetermined voltage level 69 is selected such as that indicated on waveshape G and if the voltage on the capacitor 48 attains that level 69 the indicator level sensor 24 will generate a signal indicating that the sensor 10 has not generated a waveshape 36 similar to that shown on waveshape A of

FIG. 3.

Referring to FIG. 4 there is illustrated a circuit schematic and waveforms for the thermal time constant simulator 42 of the test control circuit means 18 of FIG. 1. It is the function of the simulator 42 to develop a voltage signal after a predetermined period of time, which is not real time but operation time, to indicate that the temperature of the several components of the fuel flowing processing system including the exhaust gas and the exhaust gas sensor are sufficiently high. In particular the exhaust gas sensor 10 of the preferred embodiment must be a relatively high temperature in order to operate properly. The thermal time constant simulator 42 is essentially an asymetrical integrator having a capacitor 70, a charging resistor 71 and a discharging resistor 72 so that the charging and discharging time constants are much different. Electrically connected to the asymetrical integrator is a transistor switch member 73 which is responsive to a signal 28 representing the time that the fuel is flowing in the system. When the transistor 73 is driven into conduction, the capacitor 70 will discharge through its series resistor 72 and diode 74 combination thereby lowering the voltage level on the inverting input 75 of the comparator 46.

Referring to the waveshape A of FIG. 4 which is the input waveshape signal 28 to the base of the transistor 73, the waveshape is illustrated as being substantially a rectangular waveshape having both a varying pulse width duration and a varying time period between pulses. In the preferred embodiment the presence of a pulse indicates that the fuel is flowing through the injector into the cylinder and the absence of a pulse indicates that the injector is closed. The time duration between pulses is essentially a function of the operating speed of the engine and therefore when the engine is operating at idle speed the pulses are much further apart than when the engine is operating under load conditions. The time constant simulator 42 will not allow the capacitor 70 to discharge to an operating voltage level in Reference 76 with the engine operating continuously at idle condition. This is illustrated by the waveshape C wherein it is shown that the capacitor 70 will begin to discharge when the collector 77 of the input transistor 73 is essentially at ground level.

If the internal combustion engine is operating continuously at an idle condition it has been found that the temperature of the exhaust gas sensor 10 will decrease below a preferred operating level. The time constants of the charge and discharge circuits of the capacitor 70 of FIG. 4 are such that the voltage at the inverting input 75 of the comparator 46 will remain sufficiently close to the supply voltage thereby indicating that the system is not in condition for performing the test.

Figure 2:
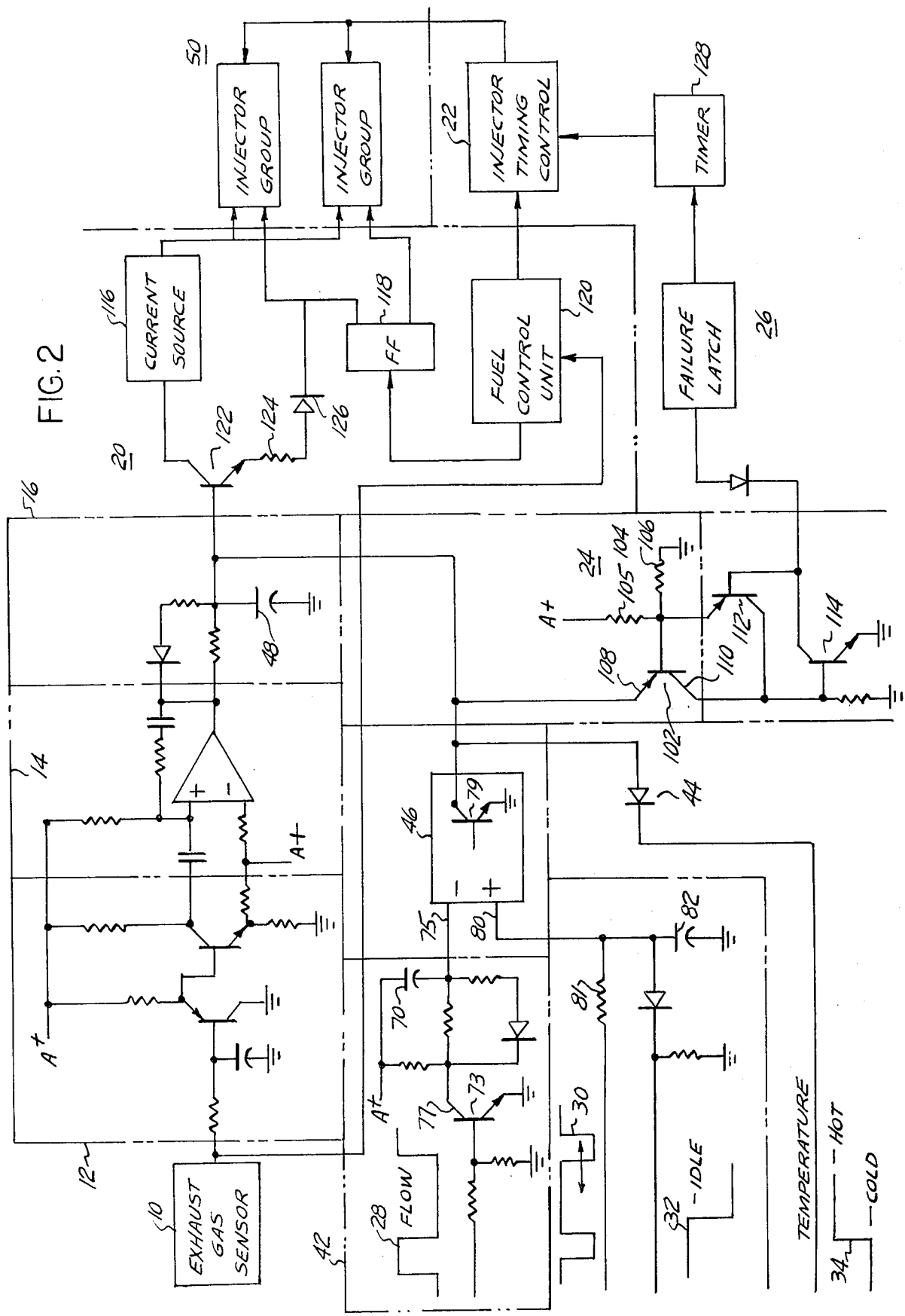
FIG. 2 is an electrical schematic of the system of FIG. 1.

In FIG. 4 the input to the noninverting input 80 of the comparator 46 is indicated as being a particular reference voltage 76 which level is in the preferred embodiment somewhat less than the supply voltage. When the voltage at the output of the capacitor 70 or at the inverting input 75 falls below the reference voltage 76 the output signal 78 of the comparator 49 will switch as shown on waveshape D. In the preferred embodiment and as illustrated in FIG. 2 the output stage 79 of the comparator 46 is an uncommitted collector of a grounded emitter NPN transistor. When the voltage on the inverting input 75 of the comparator 46 falls below the voltage level of the noninverting input 80 of the comparator 46 this output transistor 79 functioning as a clamping circuit means is turned off removing the ground clamp and essentially connects the output of the comparator 46 to the voltage level of the component electrically connected to the collector. In the preferred embodiment as illustrated in FIG. 2 this is the capacitor 48 in the transition indicator means 16, or the clamping diode 44 from the temperature circuit.

When power is initially supplied to the circuit of FIG. 4 the voltage at the output of the capacitor 70 is essentially equal to the supply voltage and will remain there until the voltage signal at the input to the transistor 73 occurs at a sufficiently fast repetition rate. The discharge time constant of the capacitor 70 in the preferred embodiment is approximately 20 seconds and the charging time constant is approximately 60 seconds. The pulse width duration of the input pulses to the transistor 73 varies in time from approximately 5 milliseconds to 15 milliseconds and the time period between pulses is typically on the order of 50 milliseconds.

It is previously indicated that one of the test conditions which is supplied to the test control circuit means 18 is an electrical signal 30 indicating the speed of the engine. As previously indicated, in the operation of the sensor detection system it is desired to test the sensor 10 and detect any failures only during idle speed conditions. The RPM signal 30 in the preferred embodiment is a series of negative pulses of a predetermined pulse time duration wherein the pulse repetition frequency or the time between the pulses varies inversely as to rpm. Thus at idle speeds the time between pulses is much longer than at high speeds. In FIG. 2 the signal 30 is supplied through a resistor 81 to a capacitor 82 and supplies or contributes to maintaining the voltage 76 on the noninverting input 80 of the comparator 46 of FIG. 4. Thus, under high speed condition, the capacitor 82 is not charged up inasmuch as the negative pulses from the rpm signal 30 occur very rapidly and operate to discharge the capacitor 82 to ground.

Figure 5:
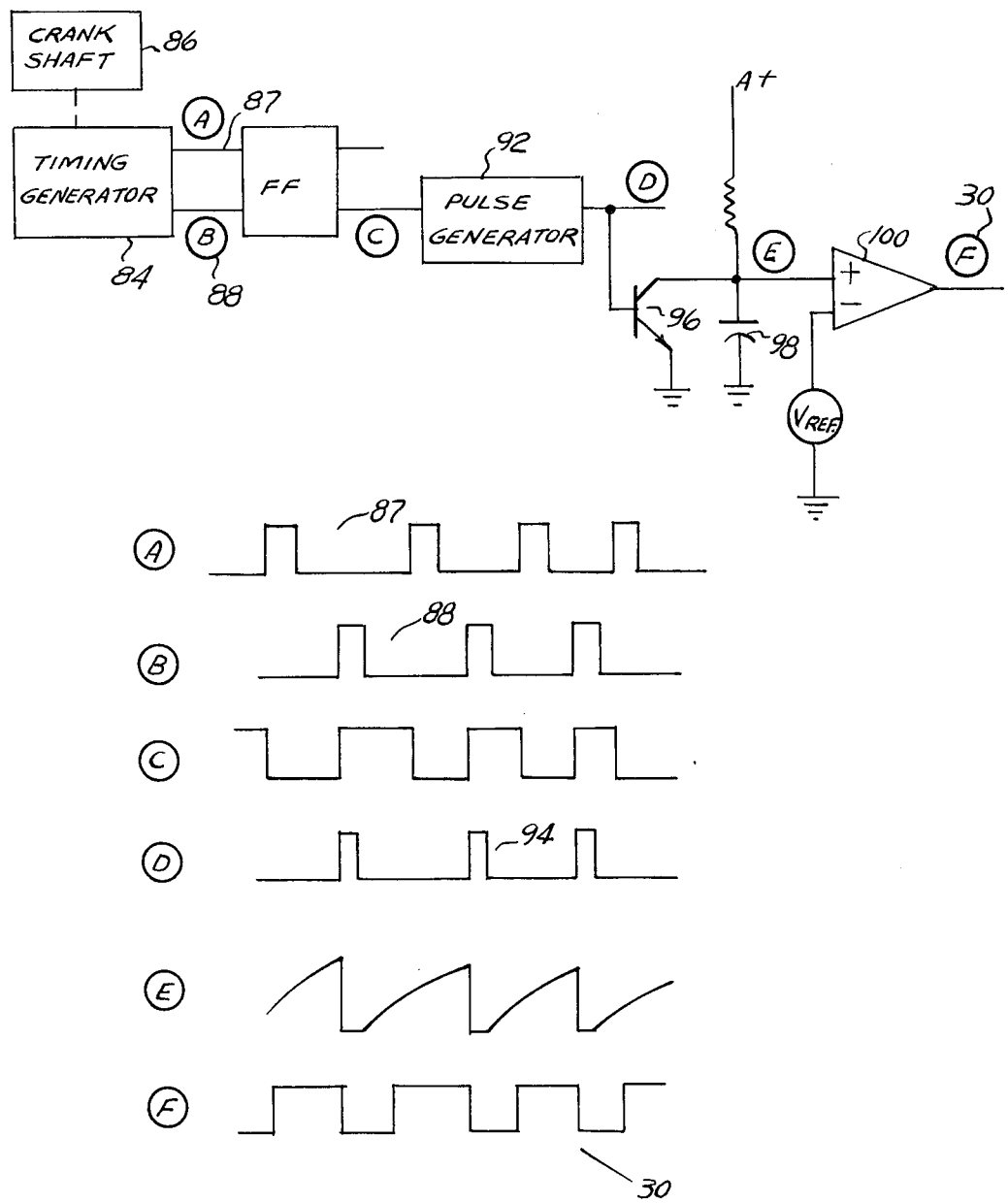
FIG. 5 is a block diagram and partial circuit schematic illustrating a generation of RPM signals for the system of FIG. 1.

Referring to FIG. 5 there is a partial block diagram and electrical schematic of the circuit for generating the rpm signal 30 as used in FIG. 2. The timing generator 84 is responsive to the rotation of the crankshaft 86 of the engine and generates a pair of pulse trains 87 and 88, labelled waveforms A and B in FIG. 5. The time between consecutive pulses in either pulse train is proportional to the speed of the crankshaft 86 and the faster the crankshaft rotates, the shorter the time or the closer together the pulses become. These pulses are supplied to a flip-flop 90 and one output is connected to a pulse generator 92 for generating pulses 94 having a predetermined width or time duration in response to the pulse trains 87 and 88 from the timing generator 84. These pulses 94 as shown in waveform D of FIG. 5 are supplied to a transistor 96 which when turned on operates to discharge a timing capacitor 98. Waveform E of FIG. 5 shows the waveform at the output of the timing capacitor 98 which is connected to noninverting input of a comparator 100. The output of the comparator 100 is a plurality of negative going pulses 30 having a predetermined pulse time duration but having a time between pulses which is inversely proportional to the speed of the engine.

Referring to FIG. 2 one of the other conditions applied to the test control circuit means 18 is an electrical signal 32 representing the position of the throttle valve in the throttle body of the engine. As previously indicated it is a function of the system to detect failures in the exhaust gas sensor 10 only during idle conditions. When the throttle is closed indicating idle condition, the voltage level on the throttle input is at a high voltage level and allows the capacitor 82 to charge to this level. As shown in FIG. 1 it is a combination of the rpm signal 30 and the throttle position signal 32 which operate to determine the idle state of the engine. In essence, these two signals 30 and 32 are combined together forming a logical AND gate.

The other test condition which must be present is the indication of the engine temperature. This signal 34 is generated by means of a coolant temperature sensor generating a high voltage output signal when the coolant exceeds a predetermined temperature. This waveshape 34 as indicated on FIG. 2, switches from a low to a high voltage level when the temperature exceeds a predetermined temperature. This signal is electrically connected to the output of the comparator by means of the clamping diode 44.

As illustrated in FIG. 2 the output of the comparator 46 in the test control circuit means 18 is an open collector NPN transistor 79. The temperature signal 34 from the coolant temperature is supplied through the clamping diode 44 to the collector of the transistor 79 clamping it to ground when the coolant temperature is below the predetermined level. However, when all the conditions for detection are present, the voltage level of the noninverting input 80 of the comparator 46 as a result of the throttle position signal 32 and the speed of the engine is high if the engine is in idle condition. When the operating temperature of the exhaust system is above a predetermined level of temperature the voltage level on the inverting input 75 of the comparator 46 is lower than the voltage level to the noninverting input 80 causing the output transistor 79 to be driven out of conduction removing the clamping voltage from the capacitor 48 in the transition interval indicator 16. This allows the capacitor 48 to charge to the output of the multivibrator 14 and when the voltage level on the capacitor 48 exceeds the predetermined level as determined by the bias voltage of the transistor 102 of the indicator level sensor 24 a failure latching signal will be generated.

Referring to FIG. 2 the indicator level sensor 24 comprises the transistor 102 having its input biased to a predetermined voltage level. This voltage level is determined by a voltage divider 104 comprising a pair of resistors 105 and 106 electrically connected across the supply voltage. In the preferred embodiment when the voltage on the emitter 108 of the transistor 102 exceeds the bias voltage on the base 109, the transistor 102 is driven into conduction and the voltage is applied to the collector 110 of the transistor 102.

The output or collector of the transistor 102 in the indicator level sensor 24 is electrically connected to a failure latching means 26 for generating a signal representing the failure of the exhaust gas sensor. The failure latching circuit comprises a pair of transistors 112 and 114 wherein the first transistor 112 has its emitter lead electrically connected to the base 109 lead of the indicator level sensor transistor 102 and its collector lead electrically connected to the collector 110 of the indicator level sensor transistor 102. The second transistor 114 has its base electrically connected to the collector of the first transistor 112 and its emitter is grounded. Thus, the two transistors 112 and 114 are connected in a latching circuit. The base of the second transistor 114 is biased through a resistor to ground therefore when the transistor 102 in the sensor circuit is driven into conduction this applies the voltage on the base lead of the second transistor 114 of the latching circuit driving it into conduction. Through the co-operation and operation of the two transistors 112 and 114 the collector lead of the second transistor 114 has a voltage level impressed thereof which will be maintained until power is removed from the circuit. This voltage level will be present regardless of succeeding operations of the transition interval indicator 16 or the test control circuit means 18.

Referring more particularly to FIG. 2, the fuel control unit 20 controls the selection of which injector group 50 is to be fired and controls the injector timing control unit 22 to determine the time duration that the injector is to be operated. A constant current source 116 is selectively coupled to each injector group 50 by means such as a flip-flop 118 receiving control signals from the control unit 120. In response to the signal on the capacitor 48 of the transition interval indicator unit 16, a control circuit represented by a transistor 122 having a resistor 124 and a diode 126 serially connected to its emitter and to the output of the flip-flop 118 provides a voltage mismatch for the current source 116 thereby effecting the amount of current supplied to the fuel control pulse generating circuitry only during the injection cycle of one of the injector groups. In the preferred embodiment this voltage mismatch circuit causes an increase in the current to the fuel control pulse generating circuitry only during the injection cycle of the one injector group thereby causing the injector group to operate on a shorter pulse width. This in effect will cause a lean fuel mixture to be injected into the cylinders controlled by the particular injector group. It is through the action of this particular circuit that will cause the exhaust gas to switch back and forth over the stoichiometric fuel air ratio.

It is further indicated in FIG. 2 the signal from the failure latching means 26 is supplied to a timer 128 whose function is to interrupt the injector timing control unit 22. In the preferred embodiment the timer will supply a signal to the injector timing control unit which in effect will drop the timing signal to one of the injector groups 50. With this timing signal not present to the injector group, fuel will not be supplied to the cylinders from the injectors controlled by that group and the internal combustion engine will then misoperate.

By unbalancing the signal to one of the injector group 50 such as removing the timing signal the internal combustion engine will operate in a rough mode which will become very annoying to the operator. However, this malfunction will only occur during idle condition and will not effect the operation of the internal combustion engine at times other than idle.

There has thus been shown and described an exhaust gas sensor operational detection system for use in a fuel injection system of an internal combustion engine. Under predetermined engine operating conditions, the detection system will detect an inoperative or failed exhaust sensor and as a result thereof will generate a failure signal for activating some from of warning means to the operator of the engine.

I claim:

1. In a fuel injection system in combination with an internal combustion engine system with electrically controlled fuel injector means and having an exhaust gas sensor generating system control signals having a first signal voltage level for one chemical composition of exhaust gas and having a second signal voltage level for another chemical composition of exhaust gas, a sensor operational detection system comprising:
- a waveshape transition detector responsive to the voltage transition of the sensor signals from the first voltage level to the second voltage level for generating a first electrical signal;
- a multivibrator responsive to said first electrical signal for generating a rectangular output pulse having a predetermined time duration independent of the time duration of said first electrical signal;
- a test control circuit means responsive to at least two predetermined engine operating conditions for generating a test enable electrical signal in response to the occurrence of said predetermined engine operating conditions;
- transition interval indicator means enabled by said test enable electrical signal and responsive to said multivibrator output signal for indicating by means of a variable voltage the interval between successive voltage transitions from said first voltage level to said second voltage level of the sensor;
- means responsive to said indicator means for varying in a predetermined relationship the electrically controlled fuel injection means for exposing the sensor to different chemical compositions of exhaust gases;
- indicator level sensor means responsive to a predetermined voltage level of said indicator means for generating a second electrical signal when the interval between successive voltage transitions from said first voltage level to said second voltage level of the sensor exceeds a predetermined interval and
- latching means responsive to said second electrical signal for generating and maintaining a failure electrical signal indicating that the sensor is misoperative.

2. In a fuel injection system according to claim 1 additionally including alarm means responsive to said failure electrical signal for generating an alarm signal when the sensor is not responding to chemical composition changes in the exhaust gas of the internal combustion engine.

3. In a fuel injection system according to claim 1 wherein said test control circuit is responsive to a throttle position sensor indicating the throttle position of the internal combustion engine and to a speed sensor indicating the operational speed of the engine.

4. In a fuel injection system according to claim 3 wherein said test control circuit generates said enable electrical signal when the engine is in an idle operating speed range.

5. In a fuel injection system according to claim 1 wherein said transition interval indicator means comprises a storage capacitor, a charging circuit electrically connected from said capacitor to said multivibrator and responsive to the voltage level output of said multivibrator between said rectangular output pulses and a discharging circuit electrically connected from said multivibrator to said capacitor and responsive to the voltage level of said rectangular pulse for discharging said capacitor.

6. In a fuel injection system according to claim 5 wherein the time constant of said charging circuit is greater than the time constant of said discharging circuit.

7. In a fuel injection system according to claim 5 wherein said charging and discharging circuits are electrically connected in parallel and said discharge circuit additionally includes diode means electrically connected for blocking the charging current to said capacitor through said discharge circuit.

8. In a fuel injection system according to claim 1 additionally including a clamping circuit means electrically connected between said test control circuit means and said transition interval indicator means for disabling said transition interval indicator means in the absence of said test enable electrical signal.

9. In a fuel injection system according to claim 8 wherein said transition interval indicator means comprises a storage capacitor and said clamping means is a grounded emitter transistor with an uncommitted collector electrically connected to said capacitor for maintaining said capacitor discharged in the absence of said test enable electrical signal.

10. In a fuel injection system according to claim 1 wherein said test control circuit means additionally includes a thermal time constant simulator means responsive to a pulsed fuel control signal indicating fuel flowing through the injector means for generating an electrical signal representing the thermal time constant of the internal combustion engine system.

11. In a fuel injection system according to claim 10 wherein said thermal time constant simulator comprises an asymetrical integrator having a charging time constant greater than the discharging time constant.

12. In a fuel injection system according to claim 11 additionally including a transistor switch means electrically connected to the discharge circuit of said asymetrical integrator and responsive to the pulse fuel control signal for enabling the discharging circuit of the capacitor means of said integrator whenever fuel is flowing through the injector means.

13. In a fuel injection system according to claim 12 wherein the capacitor means of said integrator is initially charged to a predetermined voltage level and said electrical signal representing the thermal time constant is a voltage level less than said intially charged voltage level.

14. In a fuel injection system for an internal combustion engine with electrically controlled fuel injector means, an exhaust gas sensor failure detection system comprising:
- sensor signal shaping means electrically connected to the exhaust gas sensor for generating rectangular shaped voltage waveforms having a first voltage level representing one range of exhaust gases and a second voltage level representing a second range of exhaust gases;
- means for sensing the switching of said rectangular shaped voltage waveform between said first voltage level and said second voltage level and generating a triggering signal substantially coincident with said switching;
- a multivibrator responsive to said triggering signal for generating an output pulse having a predetermined time interval;
- engine operating parameter means responsive to at least one engine operating parameter for generating a first electrical signal when the engine is operating within a predetermined range of said parameter and a second electrical signal when the engine is operating other than said predetermined range;
- capacitive means electrically responsive to said first electrical signal and to said multivibrator for charging and discharging according to the said output pulse; and capacitive charge level sensor electrically connected to said capacitive means and responsive to a predetermined charge level for generating and maintaining an exhaust gas failure detection signal.

15. An exhaust gas sensor detection system according to claim 14 further including control means responsive to said exhaust gas failure detection signal and said first electrical signal for periodically suppressing the signal to the electrically controlled fuel injection means thereby causing the internal combustion engine to malfunction.

16. An exhaust gas sensor detection system according to claim 14 wherein said engine operating parameter means is responsive to engine speeds for generating said first electrical signal indicating idle engine speed.

17. An exhaust gas sensor detection system according to claim 16 wherein said engine operating parameter means additionally includes means responsive to engine operating temperature for generating said first electrical signal indicating that the engine is at its operating temperature and operating at idle speed.

18. An exhaust gas sensor detection system according to claim 17 wherein said engine operating parameter means additionally include means responsive to the closed throttle position of said engine.

19. An exhaust gas sensor detection system according to claim 14 wherein capacitive means comprises a capacitor having separate charging and discharging circuits electrically connected in parallel circuit wherein said charging rate is substantially different than said discharging rate.

20. An exhaust gas sensor detection system according to claim 19 wherein said charging circuit comprises a resistor and said discharging circuit comprises a resistor and a diode electrically poled for discharging said capacitive means at a faster rate than the rate for charging said capacitive means.

21. An exhaust gas sensor detection system according to claim 19 wherein said second electrical signal from said engine operating parameter means maintains said capacitive means in a discharged condition and said first electrical signal enables said charging and discharging circuits.

* * * * *